United States Patent [19]

Khandke

[11] Patent Number: 5,498,536
[45] Date of Patent: Mar. 12, 1996

[54] **CHONDROITINASE II FROM *PROTEUS VULGARIS***

[75] Inventor: Kiran M. Khandke, Nanuet, N.Y.

[73] Assignee: American Cyanamid Company, Wayne, N.J.

[21] Appl. No.: 232,540

[22] Filed: Apr. 22, 1994

[51] Int. Cl.$^6$ ............... C12N 9/24; C12N 1/12; C12N 9/26; C12N 9/28

[52] U.S. Cl. ............ 435/200; 435/201; 435/202; 435/873; 435/252.1

[58] Field of Search .................... 435/183, 200, 435/201, 202, 873, 252.1

[56] References Cited

U.S. PATENT DOCUMENTS

| | | | |
|---|---|---|---|
| 4,696,816 | 9/1987 | Brown | 424/94 |
| 5,198,355 | 3/1993 | Kikuchi et al. | 435/232 |
| 5,292,509 | 3/1994 | Hageman | 424/94.61 |

FOREIGN PATENT DOCUMENTS

| | | |
|---|---|---|
| 576294 | 12/1993 | European Pat. Off. . |
| 613949 | 9/1994 | European Pat. Off. . |
| 1067253 | 5/1967 | United Kingdom . |

OTHER PUBLICATIONS

Salyers et al., Applied Environmental Microbiology, Aug. 88, 1964–9, vol. 54, No. 8.
Sato et al., Agric. Biol. Chem., 50(4), 1057–9, 1986.
Sato et al., Appl. Microbiol. Biotechnol., 1994, 41:39–46.
Kitamikado et al., Appl. Microbiol., 414–21, vol. 29, No. 3, 1975.
Yamagata et al., J. of Biol. Chem., 243(7), 1523–35, 1968.

*Primary Examiner*—David M. Naff
*Assistant Examiner*—Mike Meller
*Attorney, Agent, or Firm*—Darby & Darby

[57] ABSTRACT

A chondroitinase II is isolated from *Proteus vulgaris*. This enzyme together with chondroitinase I, is useful for selectively and completely disinserting the ocular vitreous body from the neural retina of the eye. The chondroitinase II has the amino acid sequence of SEQ. ID No. 2, an isoelectric point of from about 8.4 to about 8.45, and a molecular weight of 111,772+27 daltons as determined by electrospray and 111,725+20 daltons as determined by laser desorption. Preferably, the chondroitinase II and chondroitinase I are co-purified chondroitinases which can then be separately eluted from each other.

1 Claim, 3 Drawing Sheets

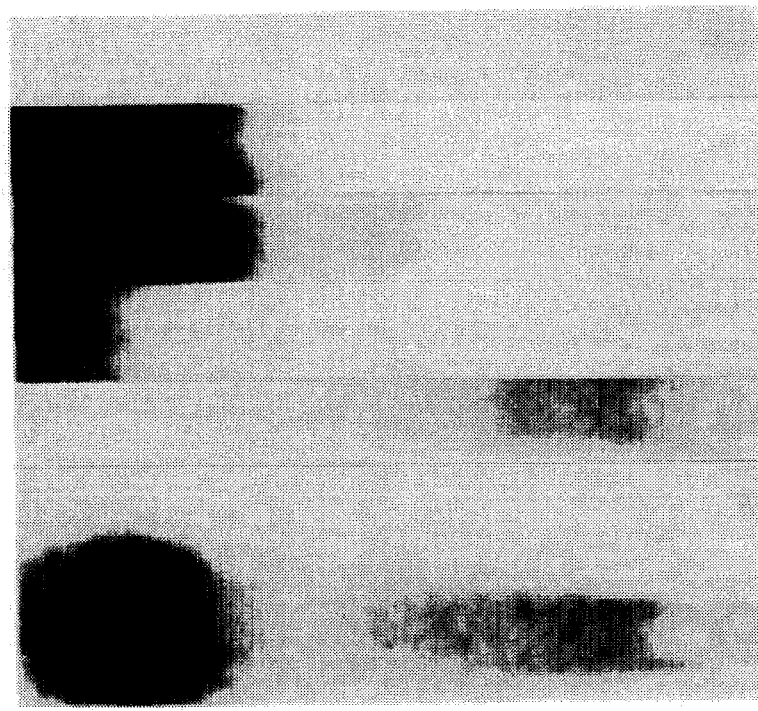
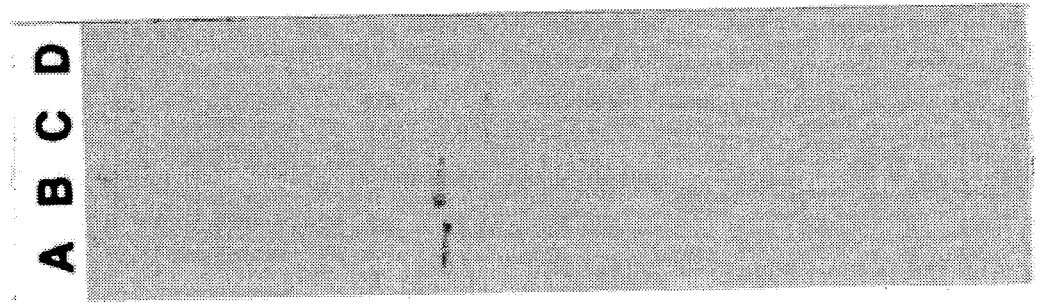

CHONDROITINASE II FROM *PROTEUS VULGARIS*

FIELD OF THE INVENTION

This invention relates to an isolated and purified chondroitinase II enzyme which, together with an isolated and purified chondroitinase I enzyme, is useful for selectively and completely disinserting the ocular vitreous body from the neural retina of the eye.

BACKGROUND OF THE INVENTION

Chondroitinases are enzymes of bacterial origin which have been described as having value in dissolving the cartilage of herniated discs without disturbing the stabilizing collagen components of those discs and in removal of the vitreous body of the eye.

Examples of chondroitinase enzymes are chondroitinase ABC, which is produced by the bacterium *Proteus vulgaris* (*P. vulgaris*), and chondroitinase AC, which is produced by *A. aurescens*. The chondroitinases function by degrading polysaccharide side chains in protein-polysaccharide complexes, without degrading the protein core.

Yamagata et al. describes the purification of the enzyme chondroitinase ABC from extracts of *P. vulgaris* (Bibliography entry 1). The enzyme selectively degrades the glycosaminoglycans chondroitin-4-sulfate, dermatan sulfate and chondroitin-6-sulfate (also referred to respectively as chondroitin sulfates A, B and C—which are side chains of proteoglycans), at pH 8 at higher rates than chondroitin or hyaluronic acid. The products of the degradation are large molecular weight unsaturated oligosaccharides and an unsaturated disaccharide. However, the enzyme did not attack keratosulfate, heparin or heparitin sulfate.

Kikuchi et al. describes the purification of glycosaminoglycan degrading enzymes, such as chondroitinase ABC, by fractionating the enzymes by adsorbing a solution containing the enzymes onto an insoluble sulfated polysaccharide carrier and then desorbing the individual enzymes from the carrier (2).

Brown describes a method for treating intervertebral disc displacement in mammals, including humans, by injecting into the intervertebral disc space effective amounts of a solution containing chondroitinase ABC (2). The chondroitinase ABC was isolated and purified from extracts of *P. vulgaris*. This native enzyme material functioned to dissolve cartilage, such as herniated spinal discs. Specifically, the enzyme causes the selective chemonucleolysis of the nucleus pulposus which contains proteoglycans and randomly dispersed collagen fibers.

Hageman describes an ophthalmic vitrectomy method for selectively and completely disinserting (removing) the ocular vitreous body, epiretinal membranes or fibrocellular membranes from the neural retina, ciliary epithelium and posterior lens surface of the mammalian eye as an adjunct to vitrectomy, by administering to the eye an effective amount of an enzyme which disrupts or degrades chondroitin sulfate proteoglycan localized specifically to sites of vitreoretinal adhesion and thereby permit complete disinsertion of said vitreous body and/or epiretinal membranes (3). The enzyme can be a protease-free glycosaminoglycanase, such as chondroitinase ABC. Hageman utilized chondroitinase ABC obtained from Seikagaku Kogyo Co., Ltd., Tokyo, Japan.

When the chondroitinase ABC enzyme is analyzed, it is found that it is actually composed of several components. The major component is a protein designated chondroitinase I. When isolated and purified chondroitinase I is used alone, it is found that only incomplete disinsertion of the vitreous body is achieved. Accordingly, there is a need to identify and characterize other component(s) necessary to achieve complete vitreal disinsertion.

SUMMARY OF THE INVENTION

Accordingly, it an object of this invention to identify and characterize component(s) in addition to the chondroitinase I protein necessary to achieve complete vitreal disinsertion.

It is a further object of this invention to demonstrate that compositions comprising the chondroitinase I protein and additional component(s) achieve complete vitreal disinsertion.

These objects are achieved by identifying and characterizing a second protein, designated chondroitinase II, having the amino-terminal amino acid sequence corresponding to amino acids numbered 1–20 of SEQ ID NO:2. In particular, the chondroitinase II protein is obtained by fermentation of the *P. vulgaris* bacterium.

This invention provides therapeutic compositions of matter useful for selectively and completely disinserting the ocular vitreous body from the neural retina of the eye, by administering to the eye an effective amount of a composition comprising an isolated and purified chondroitinase II protein having the amino-terminal amino acid sequence corresponding to amino acids numbered 1–20 of SEQ ID NO:2 and an isolated and purified chondroitinase I protein having the amino-terminal amino acid sequence corresponding to amino acids numbered 1–20 of SEQ ID NO:1.

The therapeutic compositions of this invention are administered to the eye by means of intravitreal, subvitreal, sublenticular or posterior chamber administration, and may be in the form of a pharmaceutically acceptable buffered solutions.

BRIEF DESCRIPTION OF THE FIGURES

FIG. 1 depicts an SDS-PAGE gel of a sample of chondroitinase ABC enzyme and components thereof. Lane A is the purified chondroitinase I protein; Lane B is the purified chondroitinase II protein; Lane C is a 90 kilodalton enzymatic cleavage product of chondroitinase I protein; Lane D is the chondroitinase ABC enzyme with the doublet composed of the chondroitinase I and chondroitinase II proteins.

FIG. 4 depicts the analysis by thin layer chromatography of the component peaks depicted in FIG. 3. The Lane marked "Digest" is the chondroitin sulfate material that is loaded on the GPC column as digested with chondroitinase I, prior to fractionation by GPC. The other Lanes correspond to the GPC peaks as described for FIG. 3.

DETAILED DESCRIPTION OF THE INVENTION

Figure 2:
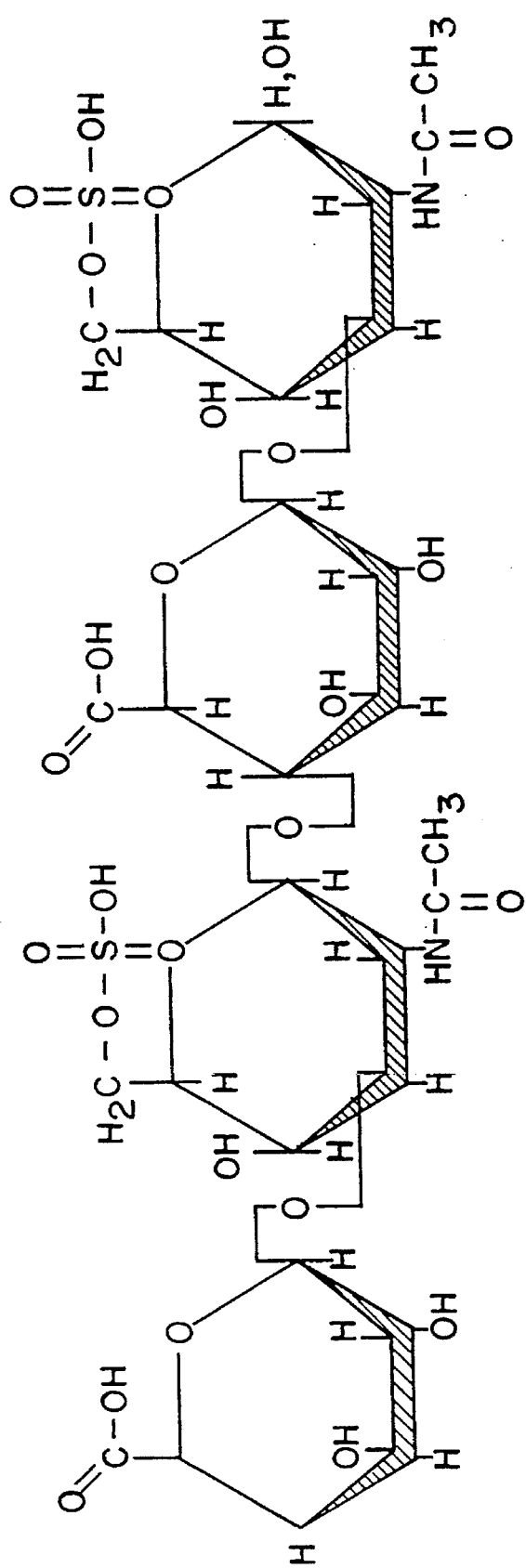
FIG. 2 depicts the 6S form of the tetrasaccharide a Δ4,5-D-glucuronic acid-β(1→3)-2-N-acetyl, 6-sulfo, D-galactosamine-β(1→4)-D-glucuronic acid-β(1→3)-2-N-acetyl, 6-sulfo, D-galactosamine.

It was previously known (4) that chondroitinase ABC, available from Seikagaku Kogyo of Tokyo, Japan, or produced by fermentation of *P. vulgaris*, degraded chondroitin sulfate. It has now been discovered that the isolation and purification of individual components of such preparations yields the chondroitinase I protein as a major component and the chondroitinase II protein as a minor component.

SDS-PAGE of the chondroitinase ABC enzyme produced by fermentation of *P. vulgaris* induced by the substrate, chondroitin sulfate, reveals a doublet band at approximately 110 kilodaltons (FIG. 1). Separation and analysis of the doublet discloses that the lower band of the doublet represents the major protein component of chondroitinase ABC, which is designated the chondroitinase I protein, while the upper band represents a second protein component, which is designated the chondroitinase II protein.

Testing of the isolated and purified native chondroitinase I and II proteins reveals that it is the combination of the two proteins which results in the complete disinsertion required for surgical vitrectomy, rather than either of the proteins individually.

Use of these two proteins provides for enzymatic disruption of the vitreoretinal interface, in particular, to enzymatic disinsertion (complete removal) of the vitreous body of the eye.

The vitreous body is a connective tissue compartment which occupies four-fifths of the volume of the eye and provides structural and metabolic support for ocular tissues, while also assisting in the maintenance of intraocular pressure and allowing light to reach the retina.

The vitreous body often forms secondary attachments to the retina at the border of degenerative or inflammatory lesions. In turn, these attachments form pivot points on the surface of the retina which often cause its detachment.

Vitrectomy is the surgical removal of a portion of the vitreous body and is indicated for the treatment or prevention of a variety of pathologic, operative or postoperative conditions which, if untreated, can result in blindness.

It is preferred that vitrectomy be carried out using a method for selectively and completely disinserting the ocular vitreous body. The method takes advantage of the knowledge that a chondroitin sulfate-containing proteoglycan is involved in vitreoretinal adhesion and that compositions which act upon the proteoglycan will result in disinsertion of the vitreous body without deleterious effects upon the rest of the eye.

One aspect of this invention comprises administering to the eye an effective amount of two chondroitinase enzymes which degrade chondrotin sulfate glycosaminoglycan/proteoglycan that is localized specifically to sites of vitreoretinal adhesion. Chondroitin sulfate is a glycosaminoglycan which is attached to a larger molecular weight proteoglycan. Chondroitin sulfate is responsible for vitreoretinal adhesion, such that degradation of chondroitin sulfate results in complete disinsertion of the vitreous body. One of these chondroitinase enzymes is the chondroitinase II form of the protein which is described herein for the first time.

Although a variety of methods can be used to isolate and purify the native chondroitinase II protein, a preferred method will now be set forth. This method first involves the copurification of chondroitinase I and chondroitinase II from the crude extract of the *P. vulgaris* fermentation mash.

It is determined that the copurification process typically results in a weight/weight ratio of approximately 60% chondroitinase I:40% chondroitinase II, although ratios of up to approximately 80% chondroitinase I:20% chondroitinase II are also obtained. The copurified proteins are then separated from each other by additional process steps.

An affinity chromatography system is used for the copurification of the chondroitinase I and chondroitinase II proteins that recognize chondroitin sulfate. First, a high capacity strong cation exchange resin is used to bind the chondroitinase I and the chondroitinase II proteins from the crude extract of the *P. vulgaris* fermentation mash. Contaminating proteins are washed from the column and are not bound to the resin. The affinity elution of the chondroitinase I and chondroitinase II proteins is accomplished with a solution of chondroitin sulfate. The coeluted proteins contain contamination of chondroitin sulfate and its digestion products.

Final copurification occurs by loading the impure mixture on a high capacity anion exchange resin. The resin binds chondroitin sulfate and its digestion products, while the chondroitinase I and the chondroitinase II proteins flow through unbound. The final copurification, when done on a large scale, is accomplished using a resin which has been charged with nickel chloride and equilibrated. The contaminating proteins flow through while the two proteins of interest bind. The chondroitinase I and chondroitinase II proteins are then eluted from the resin. While nickel salts are preferred, other salts such as zinc, copper and iron are also acceptable.

A specific advantage of this method is that the proteins are coeluted from the *P. vulgaris* fermentation mash using a very simple chromatographic system. In addition, the proteins are purified and retain their biological activity without a loss in yield or potency.

The copurified proteins are suitable for use in complete disinsertion of the vitreous body in ocular surgery. If desired, the copurified proteins are readily separated from each other by additional process steps involving further cation exchange chromatography. The individually purified proteins can be used in ratios other than those obtained by the copurification procedure.

Specifically, the copurification of the two proteins is performed as follows. The *P. vulgaris* fermentation mash is centrifuged and the resulting pellet is suspended in pH 6.8 sodium phosphate buffer and then homogenized. The pH is most preferred in the range of 6.5 to 7.0. Also preferred is the range of 5.8 to 7.4. At a pH below 5.8, there is loss of activity due to precipitation of the proteins under the acidic conditions. The loss in activity is most significant at a pH below 5. Buffers other than phosphate can also be used. The supernatant is adjusted to pH 6.8 using acetic acid and a conductivity of at least 3 mS/cm or lower. The appropriate conductivity is critical to achieve complete binding of the chondroitinase proteins to the subsequent cation exchange resin. It is determined in experiments that the conductivity must be below 3 mS/cm.

By doing these steps, the efficiency at which the chondroitinase I and chondroitinase II proteins bind to the cation exchange resin which follows in the next step is increased. Smaller amounts are bound up to a conductivity of about 4–5 mS/cm. Higher conductivities result in the majority of the proteins being lost in the unbound fraction.

The pH adjusted, clarified and homogenized liquid is loaded onto a high efficiency cation exchange resin support, Macro-Prep™ High S (Bio-Rad Laboratories, Melville, N.Y.) or other equally efficient resins. Among the charged support resin materials that are suitable for use in the present invention are other negatively charged groups, for example carboxymethyl (CM) can be also used. Several available supports can be used: e.g., Macro-Prep™ which are acrylic supports, or other commonly-used supports like dextran, agarose, polyacrylamide, silica or polymethacrylate, as long as they carry negative charges and are capable of binding to the positively charged proteins. The chondroitinase I and chondroitinase II proteins bind to the resin, while most of the protein contaminants flowthrough. The resin is washed with pH 6.8 sodium phosphate buffer to near zero optical density and then equilibrated with pH 8.3 sodium borate solution.

This pH adjustment is important to obtain an effective/specific elution in the next step. This pH is close to the optimal pH for chondroitinase activity. At this pH, there is a high degree of specific interaction between the chondroitinase proteins that are bound on the resin and the excess free substrate, causing the specific elution, while non-chondroitinase proteins (contaminants) remain bound. This pH is also close to the isoelectric point of the proteins, which allows for greater ease of elution. A pH of 8 to 9 can be used, although pH 8.3 to 8.5 gives the best results and is most particularly preferred. Other buffers in this pH range are also acceptable.

The affinity elution is accomplished with a 1% solution of chondroitin sulfate in water at a preferred pH range of 8.5 to 9. The efficiency decreases if the elution pH is below 7. The pH is adjusted with sodium hydroxide. Other alkalies can also be used. The concentration of the substrate can be as low as 0.2% and as high as 10%. However, a lower percentage results in lower yields (below 0.5%) and a higher percentage results in higher levels of contaminating proteins due to increased conductivity of the eluent. The recovery of chondroitinase activity is 72%, with a purity of 90 to 98% of the proteins being a mixture of the chondroitinase I and chondroitinase II proteins.

Although the pH of the chondroitin sulfate is adjusted, since there is no buffer in the solution (chondroitin sulfate is dissolved in deionized water), the pH is maintained close to the equilibrium pH of the resin (which is the borate buffer pH, used earlier before elution), in this case pH 8.3. The elution using the substrate results in higher purity compared to that obtained using salt solutions. In addition, salt eluted proteins require an additional desalting/diafiltration step before the next ion exchange step, which is not required for the affinity eluted proteins. This is because the conductivities needed for salt elution are about 20 fold more than 1% chondroitin sulfate solution.

The affinity eluted protein pool is simply adjusted to a pH of 6.8 with acetic acid and is loaded on a high efficiency anion exchange resin support Macro-Prep™ High Q (Bio-Rad; Q stands for quaternary ammonium) or other equally efficient resin. Other positively charged groups like DEAE can also be used.

Both the chondroitinase I and chondroitinase II proteins are eluted from the column and the chondroitin sulfate and its digestion products are bound to the resin. The resin is not only capable of removing chondroitin sulfate and increasing the purity of the product, but is also very effective in removal of endotoxin. The recovery in this step is 86% and the purity is increased to 95–99%

On a 1000 liter scale, the purity of copurified proteins after a cation exchange column and a anion exchange column is less than that obtained under laboratory scale purifications. A third chromtography step using metal chelating affinity chromatography (MCAC) is used to improve purity of the proteins. The separation is based on differing abilities of proteins to interact with chelated metal attached to an insoluble support. Proteins bind mainly because of their content of histidine or cysteine. Varying the metal ions and the pH and salt concentration of the loading buffer established conditions under which the contaminating proteins will flow through, and only the chondroitinase I and chondroitinase II proteins bind to the charged resin. By eluting with 50 mM imidazole in 50 mM tris-acetate at pH 8 in the presence of 0.2M NaCl as the elution buffer, a purity of 98% is obtained without losing in vivo activity. Imidazole is present in the protein eluted. It is separated from the protein by dialysis or diafiltration against water or a buffer.

The copurified proteins are readily separated from each other by additional process steps. The individually purified proteins can be used in ratios other than those obtained by the copurification procedure. The eluate containing the copurified chondroitinase I and chondroitinase II proteins is adjusted to a pH of 6.8. The copurified proteins are subjected to cation-exchange chromatography on Macro-Prep™ High S column, pH 6.8. The column is washed with a borate buffer, pH 8.5. The two chondroitinase proteins are eluted from the column with a NaCl gradient of 0–150 mM in borate buffer. Alternatively, a single molarity solution of 50 mM NaCl in borate buffer is also equally effective. In each case, the chondroitinase I protein elutes in earlier fractions, separated from the chondroitinase II protein, which elutes in later fractions. Amino-terminal sequencing of the purified chondroitinase I fractions yields a single sequence; and amino-terminal sequencing of the purified chondroitinase II fractions also yields a single, different sequence. Each protein is recovered at a purity of 98–99% and a yield of 85–95% from the copurified protein mixture.

The isolated and purified chondroitinase II protein of this invention is analyzed for its physical and chemical properties. Isoelectric focusing (IEF) of the chondroitinase II protein yields an isoelectric point (pI) of approximately 8.4–8.45, which is similar to that for the two isoforms of chondroitinase I, which have pIs of approximately 8.3–8.35 and 8.4–8.45, respectively.

The mass for the purified native chondroitinase II found by mass spectrometry, 111,772±27 daltons by electrospray and 111,725±20 daltons by laser desorption, corresponds to that predicted from the DNA sequence and that found for recombinant chondroitinase II. The mass for chondroitinase II is 700–800 daltons less than that for chondroitinase I, even though in an SDS-PAGE gel the chondroitinase II band is the upper band of the doublet.

However, the amino-terminal sequences of the two proteins, as well as the remainder of their amino acid sequences predicted from their nucleotide sequences, are distinct and different (compare SEQ ID NO:1 with SEQ ID NO:2).

Amino-terminal sequencing of the isolated and purified native chondroitinase II protein confirms that it has the same amino-terminal sequence as that predicted from the nucleotide sequence and determined by amino-terminal sequencing for the recombinantly-produced chondroitinase II protein. Sequencing is conducted using a ProSequencer Model 6600 (Milligen/Biosearch, Milford, MA) and following the manufacturer's instruction manual.

In particular, the first twenty residues (SEQ ID NO:2) of the amino-terminus are identical for the native and recombinant chondroitinase II. Sequencing of residues 21–40 is difficult due to increased non-specific Edman degradation. However, to the extent reliable identification of residues in this region is made, the residues are identical for the native and recombinant chondroitinase II. The same is true for sequencing of the amino-terminus of the native and recombinant chondroitinase I (SEQ ID NO:1).

Further evidence for the distinctiveness of chondroitinase I and chondroitinase II is provided by polyclonal antibody binding studies on Western blots. Chondroitinase I binds as expected to a polyclonal antibody against chondroitinase I, but does not bind (cross-react) to a polyclonal antibody against chondroitinase II. Similarly, chondroitinase II binds as expected to a polyclonal antibody against chondroitinase II, but does not bind (cross-react) to a polyclonal antibody against chondroitinase I.

Two different behaviors are observed under native and denaturing conditions. Under denaturing conditions, such as detergent treatment with SDS, there is no cross-reaction between the two chondroitinase proteins. This indicates that there are no shared (sequence-dependent) epitopes when the molecules are unfolded. Under non-denaturing conditions (native), there is evidence that at least one epitope is shared, based on antibody affinity chromatography results, where there is copurification. Without being bound by theory, this epitope could be located at the chondroitin sulfate binding/recognition site of these proteins. This region may exhibit a conserved three dimensional arrangement of amino acids which bind the chondroitin sulfate substrate. Conformational epitopes, unlike sequence-dependent epitopes, are lost when the proteins are denatured. Thus, the antibody binds only to the native, but not to the denatured proteins.

The chondroitinase II protein also has high affinity to heparin sulfate, as does chondroitinase I.

The biological activity of the chondroitinase II protein is first examined by selectively removing the chondroitinase II protein from a batch of chondroitinase ABC enzyme that had been shown previously to be active in vivo. When this batch lacking chondroitinase II is tested, it is no longer fully effective in vivo, resulting in an incomplete vitreous disinsertion.

The action of chondroitinase I and chondroitinase II upon proteoglycan is first tested in vitro using thin layer chromatography. As will be described in detail below, chondroitinase I by random endolytic cleavage generates a mixture of sugars in the initial stages. Extensive digestion by chondroitinase I generates three end products, of which one is the end product disaccharides (mainly the 6S form). However, two other digestion products are seen, the first which migrates at about one-third and the other at about two-thirds the R.F. seen for the disaccharides.

In contrast, chondroitinase II by itself does not digest proteoglycan. However, when chondroitinase II is added to chondroitinase I, neither of the two other digestion products are seen; instead, all the material is digested to completion, that is, to the disaccharides. These results are replicated when chondroitin sulfate is substituted for proteoglycan. This complete digestion is seen even at low proportions of chondroitinase II. A 90% chondroitinase I:10% chondroitinase II (w/w) mixture provides complete digestion of the proteoglycan or chondroitin sulfate to disaccharides. These results are replicated in the in vivo experiments described below. Complete vitreal disinsertion is observed only when a combination of isolated and purified chondroitinase I, together with isolated and purified chondroitinase II, is administered to the eye.

In the eye, the chondroitinase proteins degrade the chondroitin sulfate side chains of proteoglycan, but not the protein core of proteoglycan. Therefore, for in vitro studies, it is acceptable to use chondroitin sulfate instead of proteoglycan, because chondroitin sulfate is the moiety attacked by the proteins and because the cost of obtaining chondroitin sulfate is much lower than proteoglycan.

The nature of the products of the degradation of chondroitin sulfate by the chondroitinase I and chondroitinase II proteins is examined by thin layer chromatography (TLC), gel permeation chromatography (GPC) and mass spectrometry.

First, a silica gel based TLC method is developed to separate the disaccharide degradation products of chondroitin sulfate and proteoglycan and to identify the unknown sugars. The disaccharides OS, 4S and 6S are all separated. The solvent system used contains various proportions of ethyl acetate, acetic acid and water. The disaccharides are visualized by alkaline silver nitrate, which stains reducing sugars brown. Because TLC requires only 0.025 ml of sample, it allows the use of the expensive proteoglycan as a substrate, which is compared to chondroitin sulfate.

Using one dimensional TLC to analyze products, when chondroitinase I acts on proteoglycan, there are two oligosaccharides of unknown composition that are generated besides the disaccharide, which is the major product. These two oligosaccharides migrate at $\frac{1}{3}$ and $\frac{2}{3}$ the R.F. seen for the disaccharide. The $\frac{2}{3}$ R.F. sugar eventually is cleaved by the chondroitinase I, over an extended time period (at a rate at least one hundred times slower than the rate at which chondroitinase II cleaves this sugar). In contrast, the $\frac{1}{3}$ R.F. sugar is not cleaved even after an extended incubation. However, if 10% by weight of the chondroitinase I protein is substituted by the chondroitinase II protein, both the $\frac{2}{3}$ R.F. and the $\frac{1}{3}$ R.F. sugar are rapidly digested, to an extent that they do not accumulate at detectable levels.

The TLC experiment is repeated in two dimensions, first with digestion by chondroitinase I, and then with digestion by chondroitinase II. Proteoglycan is digested by chondroitinase I and then chromatographed along the first dimension of a TLC. The separated sugars are then digested with pure chondroitinase II protein on the TLC plate. The plate is now run along the second dimension under the same conditions used for the first dimension. Thus, the sugars that are not cleaved by the chondroitinase II protein migrate along the diagonal, while those that are cleaved now have altered migration characteristics of the products causing the products to migrate away from the diagonal.

The results show that all spots except the oligosaccharide migrating at about one-third the R.F. are at the diagonal. This indicates that most sugars generated by digestion of proteoglycan by chondroitinase are not further digested by the chondroitinase II protein. However, this particular oligosaccharide is completely absent from the diagonal position and instead shows two spots migrating faster, indicating that it is cleaved to two smaller saccharides.

TLC is then repeated using micro-preparative techniques to isolate these unknown sugars, by scraping and extracting them off the TLC plate. These isolated sugars are then analyzed. Ten mg of proteoglycan (ICN Biomedical Costa Mesa, CA) is digested with 8 µg of either recombinant or purified native chondroitinase I protein for 1 hour at 37° C. and the products are chromatographed on TLC plates, loading the samples as streaks. After chromatography, the silica gel is scraped from the TLC plates as bands, 5 mm apart. These silica gel pools are extracted three times using deionized water, which is expected to solubilize most of the oligosaccharide present in these fractions. These fractions are then chromatographed on TLC, to identify the fraction containing the oligosaccharide of interest. The fraction containing the disaccharide is also identified and is used as a control in subsequent experiments.

The analysis of saccharide samples (including the $\frac{1}{3}$ R.F. sugar) recovered from micropreparative TLC is not fully successful, probably because of interference from silicates extracted from the TLC plate with the sugars. The low amount of sugars recovered by this method also contributes to difficulty of further analyses. To attempt the recovery of digestion products on a larger scale would be very difficult if proteoglycan were used as substrate, because this material is expensive for small quantities and unavailable commercially in large quantities. As an alternative approach, the abundant and relatively inexpensive substrate chondroitin sulfate is used, which is contaminated with low amounts of intact and partially degraded proteoglycan. In addition, GPC is used for isolation of the sugars.

GPC provides good separation of the sugars, which are recovered in quantities suitable for analysis. In addition, silicate contamination is eliminated (unlike micro-preparative TLC). A recombinantly-expressed chondroitinase I protein is used to obtain the digest. This digest is next chromatographed using GPC. With the two native chondroitinase proteins, even using the purification method described above, trace amounts (less than 1%) of each protein are found in the other; this affects the results by decreasing the yields of the desired tetrasaccharide. It is understood that, in vivo, this is not a concern. Therefore, the native purified chondroitinase proteins are suitable for causing complete vitreal disinsertion in the eye. It is only in the in vitro studies that it is preferred to use recombinant chondroitinase I with the native chondroitinase II. Recombinant chondroitinase I is obtained by the expression in *E. coli* of the gene encoding chondroitinase I through the use of samples deposited with the American Type Culture Collection (ATCC 69234).

Figure 3:
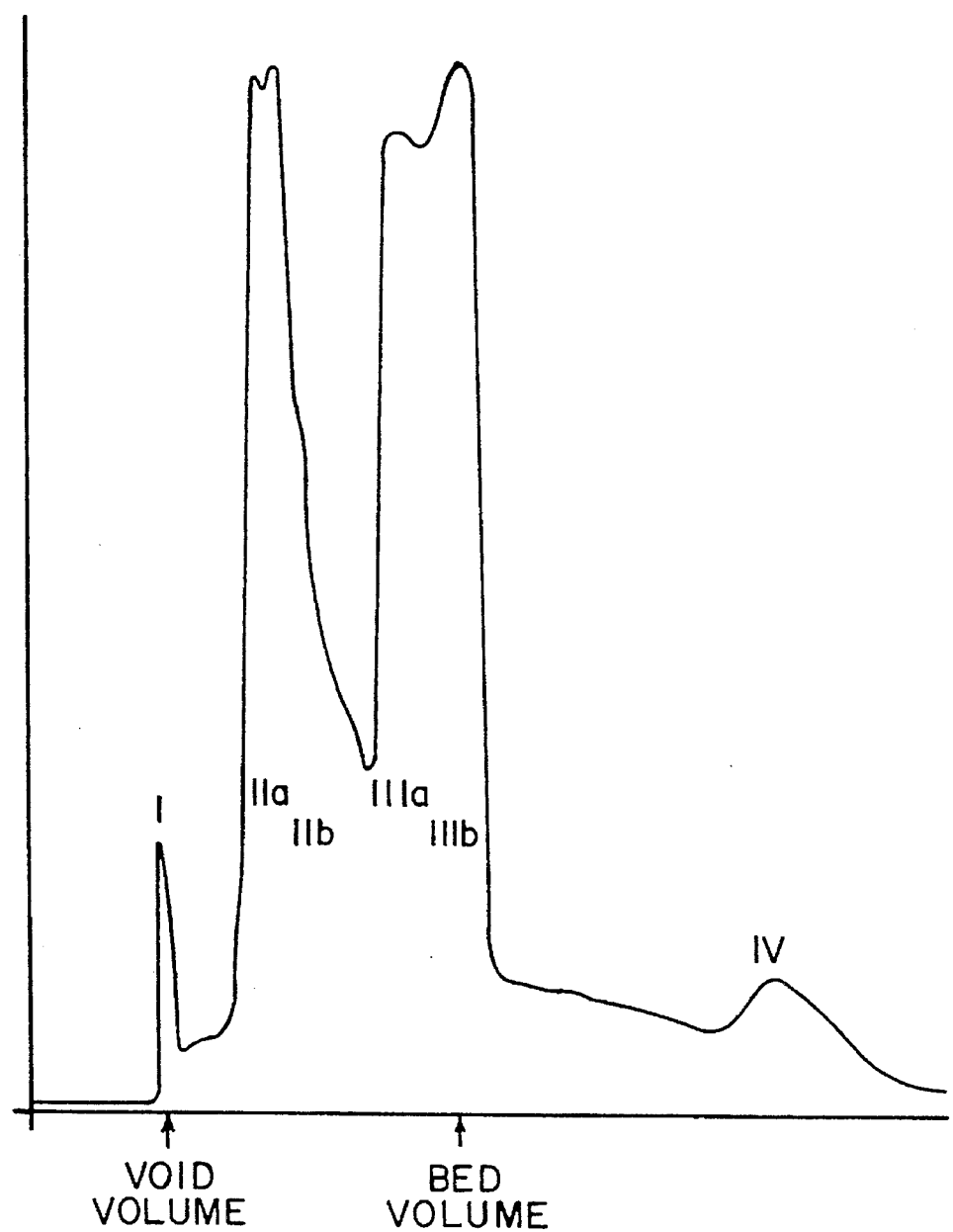
FIG. 3 depicts the component peaks of the digestion of chondroitin sulfate by chondroitinase I, as identified by gel permeation chromatography (GPC). Peak I, eluting at the void volume, is chondroitinase I. Peak II comprises two distinct components designated IIa and IIb, where IIa contains the ⅓ R.F. sugar in an enriched form, while IIb is an oversulfated disaccharide. Peak III (labelled as IIIa and IIIb) elutes close to the bed volume and consists of almost pure disaccharide. Peak IV consists of non-sugar components.

The recombinant chondroitinase I digests chondroitin sulfate into products that are recovered as four peaks from a gel permeation column (Spectra/Gel TAc, Spectrum Medical Industries Inc., Los Angeles, CA) run with 0.1% trifluoroacetic acid (TFA) as solvent. The first peak, designated I, is a small peak eluting at the void volume and does not contain any reducing sugar. It is mainly chondroitinase I. The second peak, designated II, comprises two distinct components designated IIa and IIb. IIa contains the ⅓ R.F. sugar in an enriched form, while IIb turns out to be an oversulfated disaccharide. The third peak, designated III, which is the largest, elutes close to the bed volume and consists of almost pure disaccharide. This GPC is depicted in FIG. 3 (peak III is labelled IIIa and IIIb). Peak IV consists of non-sugar components. (When this procedure is repeated on a GPC-HPLC system with small amounts of proteoglycan instead of chondroitin sulfate, similar results are obtained).

The peaks from the GPC of FIG. 3 are analyzed by TLC and the oligosaccharide of interest (Peak IIa) is found to elute with the solvent system described above, free of the major component of the digest, the disaccharides. The fractions are lyophilized to remove the TFA/water and are analyzed. Approximately one-fourth of the digested material is composed of the oligosaccharide, which is obtained as a white crystalline salt-free powder. The results of the TLC are shown in FIG. 4.

The purified oligosaccharide is incubated with different chondroitinase protein preparations, all of them being at a substrate:protein ratio of 1000:1. The pure chondroitinase II protein rapidly digests the oligosaccharide to products that migrate at the position of the disaccharides. Complete digestion is obtained at the first time point tested (15 minutes). As expected, the native chondroitinase I protein has no effect on this oligosaccharide; no disaccharide is generated even by the last time point tested (4 hours). A co-purified mixture (60:40 w/w) of the chondroitinase I and chondroitinase II proteins also cleaves this oligosaccharide, though not as rapidly as with the pure chondroitinase II protein. Significantly, the rate of cleavage of the oligosaccharide correlates quite well with the chondroitinase II protein content. This observation indicates that the oligosaccharide is useful as a specific substrate to quantitate active chondroitinase II protein, without interference from chondroitinase I.

The oligosaccharide corresponding to peak IIa is analyzed using electrospray mass spectroscopy, generating a spectrum corresponding to a mass of 918 daltons. This observed mass fits very well with the calculated mass of a tetrasaccharide of composition 'A-B-A-B', where the two sugars A and B are D-glucuronic acid and monosulfated N-acetyl D-galactosamine, respectively, which are the repeating units of chondroitin sulfate. There are several smaller peaks besides the 919 dalton (M+H) main peak, which is identified as the singly protonated sugar; their masses in order of intensity along with their tentative identification are:

839 da ($M-SO_3$): the monodesulfated sugar 901 da ($M-H_2O$): the monodehydrated sugar 941 da (M+Na): the mono sodium salt 811 da ($M-SO_3-H_2O$), 759 da ($M-2SO_3$), 741 da ($M-2SO_3-H_2O$), along with traces of other related peaks which correspond to other combinations. In addition, some minor unidentified peaks are also detected, particularly two peaks at 431 da and 531 da. The latter mass fits quite well with the expected mass of a disulfated disaccharide.

In summary, chondroitinase I partially degrades chondroitin sulfate, yielding an unsaturated disulfated tetrasaccharide with a molecular weight of 918 Daltons as calculated from its chemical formula and as observed by electrospray mass spectrometry. The structure of the major form (about 60%) of the tetrasaccharide is depicted in FIG. 2, where the sulfated side chain is at position 6 of the second and fourth rings from the left. The minor form (about 40%; not depicted) of the tetrasaccharide has this sulfated side chain at position 4 of the second and fourth rings. Both the 4S and 6S sugars are digested at similar rates by chondroitinase II to produce the disaccharides. The tetrasaccharide is referred to as Δ4,5-D-glucuronic acid-β(1→3)-2-N-acetyl, 6-sulfo, D-galactosamine-β(1→4)-D-glucuronic acid-β(1→3)-2-N-acetyl, 6-sulfo, D-galactosamine.

The tetrasaccharide is a good candidate for developing an assay for chondroitinase II, because it is resistant to cleavage by chondroitinase I (a small amount of cleavage of tetrasaccharide to disaccharide by chondroitinase I does occur, but the rate of digestion is several hundred times slower than that seen for chondroitinase II). Conversely, chondroitin sulfate is resistant to cleavage by chondroitinase II. In vitro, the tetrasaccharide is cleaved completely within a few minutes by chondroitinase II, while it is not cleaved over several hours by the same amount of chondroitinase I.

Using the foregoing information, an assay for measuring the activity of the chondroitinase II protein is developed. This assay monitors the conversion of the tetrasaccharide to the disaccharide on high performance liquid chromatography (HPLC). The chondroitinase II protein converts the tetrasaccharide to disaccharides that are separated from the substrate by HPLC on a GPC-HPLC column, such as a Shodex-OH pak KB-802 (Shoko Co. Ltd., Tokyo, Japan), using polymethacrylate as the matrix. The assay is conducted as follows. First, the tetrasaccharide substrate is prepared in a suitable solution. Pure tetrasaccharide is dissolved in water to an appropriate dilution, such as about 2 mg/ml. Preferably, the pH is adjusted to approximately 8 to 9 with an appropriate basic solvent, such as 0.1 M NaOH. A buffer, such as stock borate buffer, pH 8.5, is added to give final buffer molarity of 5 mM, pH 8.5. The volume is adjusted to give an appropriate substrate solution of tetrasaccharide, with a concentration such as 0.2–20 mg/ml.

Next, to the substrate solution is added an appropriately diluted mix of either or both of the chondroitinase proteins, such as 0.1–5 µg/ml, with a preferred dilution of 2 µg/ml. The preferred ratio of substrate solution to chondroitinase proteins is 6:1 (v/v). The assay solution is incubated at 10°–50° C., preferably 37° C., for an appropriate time, such as 15 minutes, and then chromatographed by GPC using an HPLC, such as a Shodex-OH pak KB-802.5 GPC-HPLC column (Shoko Co. Ltd., Tokyo, Japan). Other HPLC methods are also suitable, such as anion exchange, hydrophobic interaction, and reverse-phase.

The disaccharide product is detected and estimated by loading the digested substrate on a GPC-HPLC column such as described above. The mobile phase is 0.03% TFA in water. Other mobile phases can also be used, such as acetonitrile-water, or buffers like phosphate and borate. There is baseline separation of the unsaturated tetrasaccharide substrate and the disaccharide product. The relative amounts of the materials under these two peaks are estimated by a variety of conventional techniques, such as measuring the absorbance at a given wavelength, mass spectrometry, conductivity, refractive index and viscosity, and comparison to standards purified earlier and identified by TLC and other methods. It is preferred to measure the absorbance at 232 nm.

Using GPC, the tetrasaccharide elutes before the disaccharide. The tetrasaccharide is shown to be stable during the several steps of the assay, such as adjustment of the pH to 8.5 with NaOH, and incubation for short durations (up to 30 minutes) at 37° C.

Even at high ratios of substrate to chondroitinase protein, such as 20,000:1 (w/w), the purified chondroitinase II protein converts the tetrasaccharide to disaccharide at close to linear rates, at least during the initial time points. The recombinant chondroitinase I protein is not able to effect this conversion. However, as expected, a copurified mixture of chondroitinase I and chondroitinase II proteins (85:15 w/w) does catalyze this conversion. The rate of this conversion is proportionately slower than that seen for pure chondroitinase II protein, which is again as expected, in agreement with its lower content of the chondroitinase II protein.

When the concentration of chondroitinase proteins is increased one hundred fold (200:1 substrate:chondroitinase protein), both the pure chondroitinase II protein and the 85:15 co-purified protein mixture cause complete conversion to the disaccharide in 15 minutes. Even if this high concentration is used for recombinant chondroitinase I, no significant activity is detected. Thus, this in vitro assay provides a useful method for monitoring the conversion of the tetrasaccharide to the disaccharide, which is dependent only on the content of chondroitinase II. However, when the Proteus-derived chondroitinase I which contains a known contamination of the chondroitinase II protein (approximately 1 to 2%) is used alone, it does exhibit a partial conversion at this high ratio.

In vivo, the dose of the two chondroitinase proteins needed to achieve complete disinsertion of the vitreous body in the eye varies with the time of treatment. In general, the shorter the period of treatment, the larger the dose, with the limitation that the dose cannot be high enough to cause retinal or ciliary body toxicity. The treatment time can range from as short as one minute up to several hours.

Generally, between 1 and 10,000 units of a mixture of chondroitinase I and chondroitinase II proteins constitutes an effective amount of the therapeutic composition of matter useful for selectively and completely disinserting the ocular vitreous body from the neural retina of the eye. A unit is that quantity of protein that catalyzes the formation of 1 micromole of unsaturated disaccharide from chondroitin sulfate per minute at 37° C., pH 8.0. The dose is also calculated in terms of units of protein per milliliter of vitreous volume to be completely disinserted, and thus the dose can be as low as 0.05–0.1 of such units per ml.

It may be more convenient to refer to the activity of the proteins in terms of milligrams per milliliter of a pharmaceutically acceptable buffered solution. For chondroitinase I, 500 units/ml are equivalent to 1 mg protein/ml. A preferred dosage range is 1–10 mg total protein/0.4 ml buffered saline solution (BSS), with a particularly preferred dose of 4 mg total protein/0.4 ml BSS. In turn, the preferred ratios of proteins range from 90% chondroitinase I:10% chondroitinase II (w/w) to 60% chondroitinase I:40% chondroitinase II (w/w).

The chondroitinase proteins are preferably administered in a pharmaceutically acceptable buffered solution formed by mixing the concentrated proteins with a buffer solution. Any suitable buffer solution may be used, including sodium acetate, Tris, or a Balanced Salt Solution (Alcon, Fort Worth, Texas). The proteins are effective at the pH range 4.5–9.0, prefereably about pH 8.0. Therefore, the preferred pH range for buffered soltions of the proteins is approximately 7–8.

In vivo testing in monkeys demonstrates the therapeutic compositions which are one aspect of this invention. Monkeys are anesthetized and the two chondroitinase proteins are administered to the eye by means known in the art, such as intravitreal, subvitreal, sublenticular and posterior chamber administration. In one procedure, part of the vitreous body is removed by a vitrectomy instrument inserted through a first port in the eye. Light for the surgeon is provided by an endoilluminator inserted through a second port in the eye. The remainder of the vitreous body is removed by injecting the protein solution of this invention through a third port referred to as the infusion terminal. The solution diffuses through the vitreous body and the two chondroitinase proteins act to degrade the chondroitin sulfate which attaches the vitreous to the retina. After the degradation is complete, which can occur in as little as 15 minutes, the completely disinserted vitreous is removed by suction and the eye is flushed with a saline solution. A buffer solution under proper pressure is then administered through the infusion terminal. Over time, the body synthesizes the necessary molecules to essentially reconstitute the vitreous body.

The animals are sacrificed and the eyes are analyzed by such methods as visual examination, histology and pathology, sonography, transmission electron microscopy, and the use of anti-chondroitin sulfate antibodies. Where the disinsertion is incomplete, such as when only chondroitinase I is administered, some of the vitreous body in the region of the vitreous base is large enough that it can be grasped by forceps. The selectivity of the two chondroitinase proteins is demonstrated in that, when complete disinsertion is achieved, no damage to the retina is visible.

A series of monkey vitrectomy experiments is performed, testing various purified Proteus chondroitinase preparations. These experiments are summarized as follows. Monkeys receiving compositions containing both chondroitinase proteins, isolated and purified from one of several fermentation batches, have complete vitreal disinsertion. A batch which is fractionated to remove the chondroitinase II protein causes incomplete disinsertion. Histology of the tissue shows that undigested chondroitin sulfate is present if chondroitinase II is not included in the dose administered.

When purified chondroitinase II protein is added back to the fractionated batch lacking chondroitinase II (to about 12% of total protein by weight), a successful disinsertion is achieved.

Based on evaluation of these preparations by surgical criteria, it is concluded that the chondroitinase II protein plays an essential role in effecting complete vitreal disinsertion. Without the inclusion of chondroitinase II, chondroitinase I alone is ineffective in achieving complete vitreal disinsertion in the animal model.

In order that this invention may be better understood, the following examples are set forth. The examples are for the purpose of illustration only and are not to be construed as limiting the scope of the invention.

EXAMPLES

EXAMPLE 1

Isolation Of The Tetrasaccharide Substrate For Use In The Assay Of Chondroitinase Activity To 8g Chondroitin sulfate (Fluka Chemicals, Buchs, Switzerland) in 600 ml of water, pH adjusted to 8.8, with 0.1M NaOH, is added 5.8 mg of purified native chondroitinase I. Alternatively, *E. coli*-expressed recombinant chondroitinase I, available by expression of ATCC 69234, is used. The mixture is incubated at 37° C. for 3 hours and concentrated by partial lyophilization to 55 ml. The concentrate is diluted to 1:1 (v/v) with 0.1% TFA in water. The chondroitinase I digests chondroitin sulfate into products that are recovered as four peaks from a gel permeation column (Spectra/Gel TAc, Spectrum Medical Industries Inc., Los Angeles, Calif.) by eluting with 0.1% TFA as a solvent. The first peak, designated I, is a small peak eluting at the void volume, consisting of chondroitinase I, and does not contain any reducing sugar. The second peak, designated II, comprises two distinct components designated IIa and IIb. IIa contains the ⅓ R.F. sugar in an enriched form, while IIb, turns out to be an oversulfated disaccharide. The third peak, designated III, which is the largest, elutes close to the bed volume and consists of almost pure disaccharide. This GPC is depicted in FIG. 3 (peak III is labelled IIIa and IIIb). Peak IV consists of non-sugar components.

The peaks from the GPC are analyzed by TLC and the tetrasaccharide of interest (Peak IIa) is found to elute free of the major component of the digest, the disaccharides. The fractions are lyophilized to remove the TFA/water and are analyzed. Approximately one-fourth of the digested material is composed of the tetrasaccharide, as a white crystalline salt-free powder, at a yield of approximately 200 mg and a purity of approximately 95%.

EXAMPLE 2

In vitro Assay For The Activity Of The Chondroitinase II Protein In Converting The Tetrasaccharide To The Disaccharide The assay is conducted as follows. First, the tetrasaccharide substrate is prepared in a suitable solution. Pure tetrasaccharide is dissolved in water to about 2.5 mg/ml, and the pH is adjusted to approximately 8 to 9 with 0.1M NaOH. Stock borate buffer, pH 8.5, is added to give final molarity of 5 mM, pH 8.5. The volume is adjusted to give a 2 mg/ml solution of tetrasaccharide.

Next, to 60 μL of the substrate solution is added 10 μL of an appropriately diluted mix of either or both of the chondroitinase proteins, such as 0.1–5 μg/ml, with a preferred dilution of 2 μg/ml. The assay solution is incubated at 37° C. for 15 minutes and 20 μl of digested substrate is then chromatographed on GPC using an HPLC, with a Shodex-OH pak KB-802.5 GPC-HPLC column (Shoko Co. Ltd., Tokyo, Japan). The mobile phase is 0.03% TFA in water. There is baseline separation of the tetrasaccharide substrate and the disaccharide product, where the two peaks are estimated by absorbance at 232 um and comparison to standards purified earlier and identified by TLC.

Under these conditions of GPC, the tetrasaccharide elutes at about 5.2 ml, while the disaccharide elutes at about 6.3 ml, where the bed volume is about 10 ml. The tetrasaccharide is shown to be stable during the several steps of the assay, such as adjustment of the pH to 8.5 with NaOH, and incubation for short durations (up to 30 minutes) at 37° C. The assay time chosen is 15 minutes, which allows for continuous loading of freshly incubated reactions, since the run time is 12 minutes.

Even at a ratio of substrate to chondroitinase protein of 20,000:1 (w/w), the purified chondroitinase II protein converts the tetrasaccharide to disaccharide at close to linear rates, at least during the initial time points. The recombinant chondroitinase I protein is not able to effect this conversion. However, as expected, a co-purified mixture of chondroitinase I and chondroitinase II proteins (85:15 w/w) does catalyze this conversion. The rate of this conversion is much slower than that seen for pure chondroitinase II protein, which is again as expected, in agreement with its lower content of the chondroitinase II protein.

When the concentration of chondroitinase proteins is increased one hundred fold (200:1 ratio), both the pure chondroitinase II protein and the copurified protein mixture cause complete conversion to the disaccharide. Even if this high concentration is used for recombinant chondroitinase I, no significant activity is detected. However, when the Proteus-derived chondroitinase I which contains a known contamination of the chondroitinase II protein (approximately 1 to 2%) is used alone, it does exhibit a partial conversion at this high ratio. Thus, this in vitro assay provides a useful method for monitoring the conversion of the tetrasaccharide to the disaccharide by chondroitinase II.

EXAMPLE 3

Vitreal Disinsertion In Monkeys

A series of monkey vitrectomy experiments is performed, testing various purified Proteus chondroitinase preparations. Healthy monkeys are divided into five groups. Four groups receive a dose of 4 mg total chondroitinase protein in 0.4 ml BSS as follows: Group 1 receives chondroitinase I alone; Group 2 receives chondroitinase II alone; Group 3 receives a 60:40 (w/w) mixture of chondroitinase I and chondroitinase II; and Group 4 receives an 88:12 (w/w) mixture of chondroitinase I and chondroitinase II. A fifth group, Group 5, used as a negative control, receives 0.4 ml BSS only.

The monkeys are anesthetized and part of the vitreous body is removed by a vitrectomy instrument inserted through a first port in the eye. Light for the surgeon is provided by an endoilluminator inserted through a second port in the eye. The remainder of the vitreous body is removed by injecting the protein solution through a third port referred to as the infusion terminal. After the degradation, if any, is complete (15 minutes), the animals are sacrificed and the eyes are analyzed by such methods as visual examination, histology and pathology, sonography, transmission electron microscopy, and the use of anti-chondroitin sulfate antibodies.

The results are as follows:

Group 1- incomplete disinsertion

Group 2- no disinsertion

Group 3- complete disinsertion

Group 4- complete disinsertion

Group 5- no disinsertion

BIBLIOGRAPHY

1. Yamagata, T., et al., *J. Biol. Chem.*, 243, 1523–1535 (1968).
2. Kikuchi, H., et al., U.S. Pat. No. 5,198,355.
3. Brown, M.D., U.S. Pat. No. 4,696,816.
4. Hageman, G. S., U.S. Pat. No. 5,292,509.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 997 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Ala  Thr  Ser  Asn  Pro  Ala  Phe  Asp  Pro  Lys  Asn  Leu  Met  Gln  Ser  Glu
 1              5                        10                       15
Ile  Tyr  His  Phe  Ala  Gln  Asn  Asn  Pro  Leu  Ala  Asp  Phe  Ser  Ser  Asp
               20                        25                  30
Lys  Asn  Ser  Ile  Leu  Thr  Leu  Ser  Asp  Lys  Arg  Ser  Ile  Met  Gly  Asn
          35                   40                       45
Gln  Ser  Leu  Leu  Trp  Lys  Trp  Lys  Gly  Gly  Ser  Ser  Phe  Thr  Leu  His
     50                      55                  60
Lys  Lys  Leu  Ile  Val  Pro  Thr  Asp  Lys  Glu  Ala  Ser  Lys  Ala  Trp  Gly
 65                     70                   75                            80
Arg  Ser  Ser  Thr  Pro  Val  Phe  Ser  Phe  Trp  Leu  Tyr  Asn  Glu  Lys  Pro
               85                        90                       95
Ile  Asp  Gly  Tyr  Leu  Thr  Ile  Asp  Phe  Gly  Glu  Lys  Leu  Ile  Ser  Thr
              100                       105                 110
Ser  Glu  Ala  Gln  Ala  Gly  Phe  Lys  Val  Lys  Leu  Asp  Phe  Thr  Gly  Trp
         115                      120                 125
Arg  Ala  Val  Gly  Val  Ser  Leu  Asn  Asn  Asp  Leu  Glu  Asn  Arg  Glu  Met
    130                     135                 140
Thr  Leu  Asn  Ala  Thr  Asn  Thr  Ser  Ser  Asp  Gly  Thr  Gln  Asp  Ser  Ile
145                     150                 155                           160
Gly  Arg  Ser  Leu  Gly  Ala  Lys  Val  Asp  Ser  Ile  Arg  Phe  Lys  Ala  Pro
               165                      170                      175
Ser  Asn  Val  Ser  Gln  Gly  Glu  Ile  Tyr  Ile  Asp  Arg  Ile  Met  Phe  Ser
              180                       185                 190
Val  Asp  Asp  Ala  Arg  Tyr  Gln  Trp  Ser  Asp  Tyr  Gln  Val  Lys  Thr  Arg
         195                      200                205
Leu  Ser  Glu  Pro  Glu  Ile  Gln  Phe  His  Asn  Val  Lys  Pro  Gln  Leu  Pro
    210                     215                 220
Val  Thr  Pro  Glu  Asn  Leu  Ala  Ala  Ile  Asp  Leu  Ile  Arg  Gln  Arg  Leu
225                      230                 235                          240
Ile  Asn  Glu  Phe  Val  Gly  Gly  Glu  Lys  Glu  Thr  Asn  Leu  Ala  Leu  Glu
               245                      250                      255
```

-continued

| | | | | | | | | | | | | | |
|---|---|---|---|---|---|---|---|---|---|---|---|---|---|
| Glu | Asn | Ile | Ser 260 | Lys | Leu | Lys | Ser 265 | Asp | Phe | Asp | Ala | Leu | Asn Ile His 270 |
| Thr | Leu | Ala | Asn 275 | Gly | Gly | Thr | Gln 280 | Gly | Arg | His | Leu | Ile 285 | Thr Asp Lys |
| Gln | Ile | Ile | Ile 290 | Tyr | Gln | Pro 295 | Glu | Asn | Leu | Asn | Ser 300 | Gln | Asp Lys Gln |
| Leu 305 | Phe | Asp | Asn | Tyr | Val 310 | Ile | Leu | Gly | Asn | Tyr 315 | Thr | Thr | Leu Met Phe 320 |
| Asn | Ile | Ser | Arg | Ala 325 | Tyr | Val | Leu | Glu | Lys 330 | Asp | Pro | Thr | Gln Lys Ala 335 |
| Gln | Leu | Lys | Gln 340 | Met | Tyr | Leu | Leu | Met 345 | Thr | Lys | His | Leu 350 | Leu Asp Gln |
| Gly | Phe | Val 355 | Lys | Gly | Ser | Ala | Leu 360 | Val | Thr | Thr | His 365 | His | Trp Gly Tyr |
| Ser | Ser 370 | Arg | Trp | Trp | Tyr | Ile 375 | Ser | Thr | Leu | Leu | Met 380 | Ser | Asp Ala Leu |
| Lys 385 | Glu | Ala | Asn | Leu | Gln 390 | Thr | Gln | Val | Tyr | Asp 395 | Ser | Leu | Leu Trp Tyr 400 |
| Ser | Arg | Glu | Phe | Lys 405 | Ser | Ser | Phe | Asp | Met 410 | Lys | Val | Ser | Ala Asp Ser 415 |
| Ser | Asp | Leu | Asp 420 | Tyr | Phe | Asn | Thr | Leu 425 | Ser | Arg | Gln | His 430 | Leu Ala Leu |
| Leu | Leu | Leu 435 | Glu | Pro | Asp | Asp | Gln 440 | Lys | Arg | Ile | Asn | Leu 445 | Val Asn Thr |
| Phe | Ser | His 450 | Tyr | Ile | Thr | Gly 455 | Ala | Leu | Thr | Gln | Val 460 | Pro | Pro Gly Gly |
| Lys 465 | Asp | Gly | Leu | Arg | Pro 470 | Asp | Gly | Thr | Ala | Trp 475 | Arg | His | Glu Gly Asn 480 |
| Tyr | Pro | Gly | Tyr | Ser 485 | Phe | Pro | Ala | Phe | Lys 490 | Asn | Ala | Ser | Gln Leu Ile 495 |
| Tyr | Leu | Leu | Arg 500 | Asp | Thr | Pro | Phe | Ser 505 | Val | Gly | Glu | Ser 510 | Gly Trp Asn |
| Asn | Leu | Lys 515 | Lys | Ala | Met | Val | Ser 520 | Ala | Trp | Ile | Tyr | Ser 525 | Asn Pro Glu |
| Val | Gly 530 | Leu | Pro | Leu | Ala | Gly 535 | Arg | His | Pro | Phe | Asn 540 | Ser | Pro Ser Leu |
| Lys 545 | Ser | Val | Ala | Gln | Gly 550 | Tyr | Tyr | Trp | Leu | Ala 555 | Met | Ser | Ala Lys Ser 560 |
| Ser | Pro | Asp | Lys | Thr 565 | Leu | Ala | Ser | Ile | Tyr 570 | Leu | Ala | Ile | Ser Asp Lys 575 |
| Thr | Gln | Asn | Glu 580 | Ser | Thr | Ala | Ile | Phe 585 | Gly | Glu | Thr | Ile 590 | Thr Pro Ala |
| Ser | Leu | Pro 595 | Gln | Gly | Phe | Tyr | Ala 600 | Phe | Asn | Gly | Gly | Ala 605 | Phe Gly Ile |
| His | Arg 610 | Trp | Gln | Asp | Lys | Met 615 | Val | Thr | Leu | Lys | Ala 620 | Tyr | Asn Thr Asn |
| Val 625 | Trp | Ser | Ser | Glu | Ile 630 | Tyr | Asn | Lys | Asp | Asn 635 | Arg | Tyr | Gly Arg Tyr 640 |
| Gln | Ser | His | Gly | Val 645 | Ala | Gln | Ile | Val | Ser 650 | Asn | Gly | Ser | Gln Leu Ser 655 |
| Gln | Gly | Tyr | Gln 660 | Gln | Glu | Gly | Trp | Asp 665 | Trp | Asn | Arg | Met 670 | Gln Gly Ala |
| Thr | Thr | Ile 675 | His | Leu | Pro | Leu | Lys 680 | Asp | Leu | Asp | Ser | Pro 685 | Lys Pro His |

| | | | | | | | | | | | | | | |
|---|---|---|---|---|---|---|---|---|---|---|---|---|---|---|
| Thr | Leu | Met | Gln | Arg | Gly | Glu | Arg | Gly | Phe | Ser | Gly | Thr | Ser | Ser | Leu |
| | 690 | | | | | 695 | | | | | 700 | | | |
| Glu | Gly | Gln | Tyr | Gly | Met | Met | Ala | Phe | Asp | Leu | Ile | Tyr | Pro | Ala | Asn |
| 705 | | | | | 710 | | | | | 715 | | | | | 720 |
| Leu | Glu | Arg | Phe | Asp | Pro | Asn | Phe | Thr | Ala | Lys | Lys | Ser | Val | Leu | Ala |
| | | | | 725 | | | | | 730 | | | | | 735 | |
| Ala | Asp | Asn | His | Leu | Ile | Phe | Ile | Gly | Ser | Asn | Ile | Asn | Ser | Ser | Asp |
| | | | 740 | | | | | 745 | | | | | 750 | | |
| Lys | Asn | Lys | Asn | Val | Glu | Thr | Thr | Leu | Phe | Gln | His | Ala | Ile | Thr | Pro |
| | | 755 | | | | | 760 | | | | | 765 | | | |
| Thr | Leu | Asn | Thr | Leu | Trp | Ile | Asn | Gly | Gln | Lys | Ile | Glu | Asn | Met | Pro |
| | 770 | | | | | 775 | | | | | 780 | | | | |
| Tyr | Gln | Thr | Thr | Leu | Gln | Gln | Gly | Asp | Trp | Leu | Ile | Asp | Ser | Asn | Gly |
| 785 | | | | | 790 | | | | | 795 | | | | | 800 |
| Asn | Gly | Tyr | Leu | Ile | Thr | Gln | Ala | Glu | Lys | Val | Asn | Val | Ser | Arg | Gln |
| | | | | 805 | | | | | 810 | | | | | 815 | |
| His | Gln | Val | Ser | Ala | Glu | Asn | Lys | Asn | Arg | Gln | Pro | Thr | Glu | Gly | Asn |
| | | | 820 | | | | | 825 | | | | | 830 | | |
| Phe | Ser | Ser | Ala | Trp | Ile | Asp | His | Ser | Thr | Arg | Pro | Lys | Asp | Ala | Ser |
| | | 835 | | | | | 840 | | | | | 845 | | | |
| Tyr | Glu | Tyr | Met | Val | Phe | Leu | Asp | Ala | Thr | Pro | Glu | Lys | Met | Gly | Glu |
| | 850 | | | | | 855 | | | | | 860 | | | | |
| Met | Ala | Gln | Lys | Phe | Arg | Glu | Asn | Asn | Gly | Leu | Tyr | Gln | Val | Leu | Arg |
| 865 | | | | | 870 | | | | | 875 | | | | | 880 |
| Lys | Asp | Lys | Asp | Val | His | Ile | Ile | Leu | Asp | Lys | Leu | Ser | Asn | Val | Thr |
| | | | | 885 | | | | | 890 | | | | | 895 | |
| Gly | Tyr | Ala | Phe | Tyr | Gln | Pro | Ala | Ser | Ile | Glu | Asp | Lys | Trp | Ile | Lys |
| | | | 900 | | | | | 905 | | | | | 910 | | |
| Lys | Val | Asn | Lys | Pro | Ala | Ile | Val | Met | Thr | His | Arg | Gln | Lys | Asp | Thr |
| | | 915 | | | | | 920 | | | | | 925 | | | |
| Leu | Ile | Val | Ser | Ala | Val | Thr | Pro | Asp | Leu | Asn | Met | Thr | Arg | Gln | Lys |
| | 930 | | | | | 935 | | | | | 940 | | | | |
| Ala | Ala | Thr | Pro | Val | Thr | Ile | Asn | Val | Thr | Ile | Asn | Gly | Lys | Trp | Gln |
| 945 | | | | | 950 | | | | | 955 | | | | | 960 |
| Ser | Ala | Asp | Lys | Asn | Ser | Glu | Val | Lys | Tyr | Gln | Val | Ser | Gly | Asp | Asn |
| | | | | 965 | | | | | 970 | | | | | 975 | |
| Thr | Glu | Leu | Thr | Phe | Thr | Ser | Tyr | Phe | Gly | Ile | Pro | Gln | Glu | Ile | Lys |
| | | | 980 | | | | | 985 | | | | | 990 | | |
| Leu | Ser | Pro | Leu | Pro | | | | | | | | | | | |
| | | 995 | | | | | | | | | | | | | |

( 2 ) INFORMATION FOR SEQ ID NO:2:

( i ) SEQUENCE CHARACTERISTICS:
        ( A ) LENGTH: 990 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Leu | Pro | Thr | Leu | Ser | His | Glu | Ala | Phe | Gly | Asp | Ile | Tyr | Leu | Phe | Glu |
| 1 | | | | 5 | | | | | 10 | | | | | 15 | |
| Gly | Glu | Leu | Pro | Asn | Thr | Leu | Thr | Thr | Ser | Asn | Asn | Gln | Leu | Ser | |
| | | | 20 | | | | | 25 | | | | | 30 | | |
| Leu | Ser | Lys | Gln | His | Ala | Lys | Asp | Gly | Glu | Gln | Ser | Leu | Lys | Trp | Gln |

|    |    |    |    |    | 35  |    |    |    |    | 40  |    |    |    |    | 45  |    |    |    |    |
|----|----|----|----|----|-----|----|----|----|----|-----|----|----|----|----|-----|----|----|----|----|

Tyr Gln Pro Gln Ala Thr Leu Thr Leu Asn Asn Ile Val Asn Tyr Gln
         50                      55                      60

Asp Asp Lys Asn Thr Ala Thr Pro Leu Thr Phe Met Met Trp Ile Tyr
 65                      70                      75                      80

Asn Glu Lys Pro Gln Ser Ser Pro Leu Thr Leu Ala Phe Lys Gln Asn
                 85                      90                              95

Asn Lys Ile Ala Leu Ser Phe Asn Ala Glu Leu Asn Phe Thr Gly Trp
                100                     105                     110

Arg Gly Ile Ala Val Pro Phe Arg Asp Met Gln Gly Ser Ala Thr Gly
            115                     120                     125

Gln Leu Asp Gln Leu Val Ile Thr Ala Pro Asn Gln Ala Gly Thr Leu
        130                     135                     140

Phe Phe Asp Gln Ile Ile Met Ser Val Pro Leu Asp Asn Arg Trp Ala
145                     150                     155                     160

Val Pro Asp Tyr Gln Thr Pro Tyr Val Asn Asn Ala Val Asn Thr Met
                    165                     170                     175

Val Ser Lys Asn Trp Ser Ala Leu Met Tyr Asp Gln Met Gln Phe Gln
                180                     185                     190

Ala His Tyr Pro Thr Leu Asn Phe Asp Thr Glu Phe Arg Asp Asp Gln
            195                     200                     205

Thr Glu Met Ala Ser Ile Tyr Gln Arg Phe Glu Tyr Tyr Gln Gly Ile
        210                     215                     220

Arg Ser Asp Lys Lys Ile Thr Pro Asp Met Leu Asp Lys His Leu Ala
225                     230                     235                     240

Leu Trp Glu Lys Leu Val Leu Thr Gln His Ala Asp Gly Ser Ile Thr
                    245                     250                     255

Gly Lys Ala Leu Asp His Pro Asn Arg Gln His Phe Met Lys Val Glu
                260                     265                     270

Gly Val Phe Ser Glu Gly Thr Gln Lys Ala Leu Leu Asp Ala Asn Met
            275                     280                     285

Leu Arg Asp Val Gly Lys Thr Leu Leu Gln Thr Ala Ile Tyr Leu Arg
        290                     295                     300

Ser Asp Ser Leu Ser Ala Thr Asp Arg Lys Lys Leu Glu Glu Arg Tyr
305                     310                     315                     320

Leu Leu Gly Thr Arg Tyr Val Leu Glu Gln Gly Phe Thr Arg Gly Ser
                    325                     330                     335

Gly Tyr Gln Ile Ile Thr His Val Gly Tyr Gln Thr Arg Glu Leu Phe
                340                     345                     350

Asp Ala Trp Phe Ile Gly Arg His Val Leu Ala Lys Asn Asn Leu Leu
            355                     360                     365

Ala Pro Thr Gln Gln Ala Met Met Trp Tyr Asn Ala Thr Gly Arg Ile
        370                     375                     380

Phe Glu Lys Asn Asn Glu Ile Val Asp Ala Asn Val Asp Ile Leu Asn
385                     390                     395                     400

Thr Gln Leu Gln Trp Met Ile Lys Ser Leu Leu Met Leu Pro Asp Tyr
                    405                     410                     415

Gln Gln Arg Gln Gln Ala Leu Ala Gln Leu Gln Ser Trp Leu Asn Lys
            420                     425                     430

Thr Ile Leu Ser Ser Lys Gly Val Ala Gly Gly Phe Lys Ser Asp Gly
        435                     440                     445

Ser Ile Phe His His Ser Gln His Tyr Pro Ala Tyr Ala Lys Asp Ala
    450                     455                     460

```
Phe  Gly  Gly  Leu  Ala  Pro  Ser  Val  Tyr  Ala  Leu  Ser  Asp  Ser  Pro  Phe
465                      470                      475                      480

Arg  Leu  Ser  Thr  Ser  Ala  His  Glu  Arg  Leu  Lys  Asp  Val  Leu  Leu  Lys
                    485                      490                      495

Met  Arg  Ile  Tyr  Thr  Lys  Glu  Thr  Gln  Ile  Pro  Val  Val  Leu  Ser  Gly
                500                      505                      510

Arg  His  Pro  Thr  Gly  Leu  His  Lys  Ile  Gly  Ile  Ala  Pro  Phe  Lys  Trp
               515                      520                      525

Met  Ala  Leu  Ala  Gly  Thr  Pro  Asp  Gly  Lys  Gln  Lys  Leu  Asp  Thr  Thr
          530                      535                      540

Leu  Ser  Ala  Ala  Tyr  Ala  Lys  Leu  Asp  Asn  Lys  Thr  His  Phe  Glu  Gly
545                      550                      555                      560

Ile  Asn  Ala  Glu  Ser  Glu  Pro  Val  Gly  Ala  Trp  Ala  Met  Asn  Tyr  Ala
                565                      570                      575

Ser  Met  Ala  Ile  Gln  Arg  Arg  Ala  Ser  Thr  Gln  Ser  Pro  Gln  Gln  Ser
               580                      585                      590

Trp  Leu  Ala  Ile  Ala  Arg  Gly  Phe  Ser  Arg  Tyr  Leu  Val  Gly  Asn  Glu
          595                      600                      605

Ser  Tyr  Glu  Asn  Asn  Asn  Arg  Tyr  Gly  Arg  Tyr  Leu  Gln  Tyr  Gly  Gln
     610                      615                      620

Leu  Glu  Ile  Ile  Pro  Ala  Asp  Leu  Thr  Gln  Ser  Gly  Phe  Ser  His  Ala
625                      630                      635                      640

Gly  Trp  Asp  Trp  Asn  Arg  Tyr  Pro  Gly  Thr  Thr  Ile  His  Leu  Pro
                    645                      650                      655

Tyr  Asn  Glu  Leu  Glu  Ala  Lys  Leu  Asn  Gln  Leu  Pro  Ala  Ala  Gly  Ile
               660                      665                      670

Glu  Glu  Met  Leu  Leu  Ser  Thr  Glu  Ser  Tyr  Ser  Gly  Ala  Asn  Thr  Leu
          675                      680                      685

Asn  Asn  Asn  Ser  Met  Phe  Ala  Met  Lys  Leu  His  Gly  His  Ser  Lys  Tyr
     690                      695                      700

Gln  Gln  Gln  Ser  Leu  Arg  Ala  Asn  Lys  Ser  Tyr  Phe  Leu  Phe  Asp  Asn
705                      710                      715                      720

Arg  Val  Ile  Ala  Leu  Gly  Ser  Gly  Ile  Glu  Asn  Asp  Asp  Lys  Gln  His
                    725                      730                      735

Thr  Thr  Glu  Thr  Thr  Leu  Phe  Gln  Phe  Ala  Val  Pro  Lys  Leu  Gln  Ser
               740                      745                      750

Val  Ile  Ile  Asn  Gly  Lys  Lys  Val  Asn  Gln  Leu  Asp  Thr  Gln  Leu  Thr
          755                      760                      765

Leu  Asn  Asn  Ala  Asp  Thr  Leu  Ile  Asp  Pro  Ala  Gly  Asn  Leu  Tyr  Lys
     770                      775                      780

Leu  Thr  Lys  Gly  Gln  Thr  Val  Lys  Phe  Ser  Tyr  Gln  Lys  Gln  His  Ser
785                      790                      795                      800

Leu  Asp  Asp  Arg  Asn  Ser  Lys  Pro  Thr  Glu  Gln  Leu  Phe  Ala  Thr  Ala
                    805                      810                      815

Val  Ile  Ser  His  Gly  Lys  Ala  Pro  Ser  Asn  Glu  Asn  Tyr  Glu  Tyr  Ala
               820                      825                      830

Ile  Ala  Ile  Glu  Ala  Gln  Asn  Asn  Lys  Ala  Pro  Glu  Tyr  Thr  Val  Leu
          835                      840                      845

Gln  His  Asn  Asp  Gln  Leu  His  Ala  Val  Lys  Asp  Lys  Ile  Thr  Gln  Glu
     850                      855                      860

Glu  Gly  Tyr  Ala  Phe  Phe  Glu  Ala  Thr  Lys  Leu  Lys  Ser  Ala  Asp  Ala
865                      870                      875                      880

Thr  Leu  Leu  Ser  Ser  Asp  Ala  Pro  Val  Met  Val  Met  Ala  Lys  Ile  Gln
                    885                      890                      895
```

| | | | | | | | | | | | | | | |
|---|---|---|---|---|---|---|---|---|---|---|---|---|---|---|
| Asn | Gln | Gln | Leu<br>900 | Thr | Leu | Ser | Ile | Val<br>905 | Asn | Pro | Asp | Leu | Asn<br>910 | Leu | Tyr |
| Gln | Gly | Arg<br>915 | Glu | Lys | Asp | Gln | Phe<br>920 | Asp | Asp | Lys | Gly | Asn<br>925 | Gln | Ile | Glu |
| Val | Ser<br>930 | Val | Tyr | Ser | Arg | His<br>935 | Trp | Leu | Thr | Ala | Glu<br>940 | Ser | Gln | Ser | Thr |
| Asn<br>945 | Ser | Thr | Ile | Thr | Val<br>950 | Lys | Gly | Ile | Trp | Lys<br>955 | Leu | Thr | Thr | Pro | Gln<br>960 |
| Pro | Gly | Val | Ile | Ile<br>965 | Lys | His | His | Asn | Asn<br>970 | Asn | Thr | Leu | Ile | Thr<br>975 | Thr |
| Thr | Thr | Ile | Gln<br>980 | Ala | Thr | Pro | Thr | Val<br>985 | Ile | Asn | Leu | Val | Lys<br>990 | | |

What is claimed is:

1. A purified chondroitinase II protein having the amino acid sequence of SEQ ID NO:2.

* * * * *